United States Patent [19]
Jarvik

[11] Patent Number: 5,948,677
[45] Date of Patent: Sep. 7, 1999

[54] READING FRAME INDEPENDENT EPITOPE TAGGING

[76] Inventor: Jonathan W. Jarvik, 7903 Caminito del Cid, La Jolla, Calif. 92037

[21] Appl. No.: 08/762,106

[22] Filed: Dec. 9, 1996

[51] Int. Cl.[6] ............................ C12N 15/63; C12N 15/85; C07H 21/04
[52] U.S. Cl. ...................... 435/325; 435/69.1; 435/172.3; 435/252.3; 435/320.1; 435/410; 536/23.1; 536/24.3
[58] Field of Search ................................ 435/6, 69.3, 69.7, 435/91.1, 69.1, 172.1, 172.3, 320.1, 325, 355, 252.3, 252.33, 410; 536/23.1, 23.4, 24.3, 24.5

[56] References Cited

U.S. PATENT DOCUMENTS 5,612,180  3/1997  Brown et al. ................................ 435/6
5,652,128  7/1997  Jarvik ........................................... 435/6

OTHER PUBLICATIONS

Vinay Kumar, Basic Immunology, in "Pathologic Basis of Disease" by Robbins and Cotran, 2d Ed., pp. 262–263 (1979).

Lehninger, Biochemistry, 1st Ed, pp. 652–654, 691–692, 717–718 (1970).

*Primary Examiner*—John L. LeGuyader
*Assistant Examiner*—Mark L. Shibuya
*Attorney, Agent, or Firm*—Harris F. Brotman

[57] ABSTRACT

Oligonucleotide sequence comprising a repeating nucleotide sequence encoding circularly permuted epitope tag, and vectors comprising the oligonucleotide sequences. Methods for using the sequences to tag proteins. Antibodies specific for the epitopes. Methods for detecting and purifying proteins.

11 Claims, 4 Drawing Sheets

FIG. 1A

```
ATGGTGCAGGCTAAGGCGCAGCAGCAGCTGTACACGCACGCTGCAGAGCCGAAGGCAGTTC
AACAGCGGCGTGCCAAGTATCGCGAGGATGAGACGACGCAGACGCTGCCCACGGCAAACAT
CATGTTCGACCGTCGTGTAGTACGAGGCAACACATACGCCGCGCGCATTCTGCCCGCCGAT
GCCACGCAAACGCAAACCAAGGGACCCTCGCCGGCATCGACGAAGAAGAGGACAACACGGA
CGCTGCCGCCCCGGACGCCGGAGGCCGTTGACGGCCGGCGGCACATCGACATCCAAACGGA
CGTGTATCTGGAGGAGCTGACAGACACCGTGCCGGAGGCTGACACCTCCACGCAGACCGAT
GCCTTCCTGGACCGGCCCCCCACCCCGCTGTTTGTGCCGCAGAAGACGGGCACGGACGCCA
TCACCCAGATCGAGAACGGTGACCTGTTTGACTTTGACTTCGAGGTGGAGCCCATCCTGGA
GGTGCTGGTGGGCAAGGTGCTGGAGCAGGGCCTGATGGAGGTGCTGGAGGAGGAGGAGCTG
GCGGCCATGCGCGCGCACCAGGAGCACTTCGAGCAGATTCGCAACGCCGAGCTGGTGGCCA
CACAGCGCATGGAGGCGGCGGAGCGGCGCAAGCTGGAGGAGAAGGAGCGGCGCATGCAGCA
GGAGCGCGAGCGTGTCGAGCGCGAGCGCGTGGTGCGCCAGAAGGTGGCGGCCAGCGCCTTT
GCGCGCGGCTACCTGTCTGGCATTGTCAACACGGTGTTTGACCGCTTGGTGTCCAGCGGCT
ACATCTACGACCCCGTCATGCGCGAGGTGGAGACGGCGTTCATGCCCTGGCTCAAGGAGCA
GGCCATCGGCTACCTGGCGCGCGGCGTGGTGGCGCGGCGCGTGGTGGACAAGCTGGTGGAG
GACGCGGCGGCGGCGCTGGCAGCCAATCGCAGCACCCTGGCGGACAAGGCCGCCAGCACGG
CGGCCACGGTGGACGCCTGGGCGGAGCGGCAGGCCAAGATGGAGGCGGAGCTGCAAGGCAA
GGAGCTGGAGGCGGTGCGGCGGCGGCCCACGTTTGTGCTGCGCGAGCTCAAGCCCGCGGTG
GCGAGCGCCGATGCCGTCGAGGCGGCGGCCGCGGAGCTGACGGCGCAGGCGGAGGAGGCGG
CCAACGCCAAGTGGGAGGCGGACAAGGCGGAGGCGGCGGAGAAGGCGCGCGCCGAGGCGGA
GGCGGCGGCGGAGGAGCAGAAGGCGCTGCTGGAGGAGTTGGCGGCCACGGCGGCGGCGGAG
GCGGAGGAGCGCGGCGAGGAGCCGCCGGCGGAGCCGCCGTCGCTGCCGGATGGCGTGGAGC
CTGTGGACGTGGAGGCTGAGGTGGCCAAGGCGGTGGAGGCTGTGCCCAAGCCGCCGGTCAA
GGAGGTGACAGACATTGACATCCTGTCGTACATGATGGACAAGGGTGCCATCACCAAGGAC
GCCATCATCCAGGCGCTGGCGGTGCACGCGCTGGGCGACAAGGCCTACACCAACCACCCCG
CGTTCGCCGAGGCGGAGGGCGCG
```

FIG. 1B

ATGGTGCAGGCTAAGGCGCAGCAGCAGCTGTACACGCACGCTGCAGAGCCGAAGGCAGTTC
AACAGCGGCGTGCCAAGTATCGCGAGGATGAGACGACGCAGACGCTGCCCACGGCAAACAT
CATGTTCGACCGTCGTGTAGTACGAGGCAACACATACGCCGCGCGCATTCTGCCCGCCGAT
GCCACGCAAACGCAAACCAAGGGACCCTCGCCGGCATCGACGAAGAAGAGGACAACACGGA
CGCTGCCGCCCCGGACGCCGGAGGCCGTTGACGGCCGGCGGCACATCGACATCCAAACGGA
CGTGTATCTGGAGGAGCTGACAGACACCGTGCCGGAGGCTGACACCTCCACGCAGACCGAT
GCCTTCCTGGACCGGCCCCCCACCCCGCTGTTTGTGCCGCAGAAGACGGGCACGGACGCCA
TCACCCAGATCACAGACAGACAGACAGACAGACAGACAGGGATCGAGAACGGTGAC
CTGTTTGACTTTGACTTCGAGGTGGAGCCCATCCTGGAGGTGCTGGTGGGCAAGGTGCTGG
AGCAGGGCCTGATGGAGGTGCTGGAGGAGGAGGAGCTGGCGGCCATGCGCGCGCACCAGGA
GCACTTCGAGCAGATTCGCAACGCCGAGCTGGTGGCCACACAGCGCATGGAGGCGGCGGAG
CGGCGCAAGCTGGAGGAGAAGGAGCGGCGCATGCAGCAGGAGCGCGAGCGTGTCGAGCGCG
AGCGCGTGGTGCGCCAGAAGGTGGCGGCCAGCGCCTTTGCGCGCGGCTACCTGTCTGGCAT
TGTCAACACGGTGTTTGACCGCTTGGTGTCCAGCGGCTACATCTACGACCCCGTCATGCGC
GAGGTGGAGACGGCGTTCATGCCCTGGCTCAAGGAGCAGGCCATCGGCTACCTGGCGCGCG
GCGTGGTGGCGCGGCGCGTGGTGGACAAGCTGGTGGAGGACGCGGCGGCGGCGCTGGCAGC
CAATCGCAGCACCCTGGCGGACAAGGCCGCCAGCACGGCGGCCACGGTGGACGCCTGGGCG
GAGCGGCAGGCCAAGATGGAGGCGGAGCTGCAAGGCAAGGAGCTGGAGGCGGTGCGGCGGC
GGCCCACGTTTGTGCTGCGCGAGCTCAAGCCCGCGGTGGCGAGCGCCGATGCCGTCGAGGC
GGCGGCCGCGGAGCTGACGGCGCAGGCGGAGGAGGCGGCCAACGCCAAGTGGGAGGCGGAC
AAGGCGGAGGCGGCGGAGAAGGCGCGCGCCGAGGCGGAGGCGGCGGCGGAGGAGCAGAAGG
CGCTGCTGGAGGAGTTGGCGGCCACGGCGGCGGCGGAGGCGGAGGAGCGCGGCGAGGAGCC
GCCGGCGGAGCCGCCGTCGCTGCCGGATGGCGTGGAGCCTGTGGACGTGGAGGCTGAGGTG
GCCAAGGCGGTGGAGGCTGTGCCCAAGCCGCCGGTCAAGGAGGTGACAGACATTGACATCC
TGTCGTACATGATGGACAAGGGTGCCATCACCAAGGACGCCATCATCCAGGCGCTGGCGGT
GCACGCGCTGGGCGACAAGGCCTACACCAACCACCCCGCGTTCGCCGAGGCGGAGGGCGCG

FIG. 2A

MVQAKAQQQLYTHAAEPKAVQQRRAKYREDETTQTLPTANIMFDRRVVRGNTYAARILPAD
ATQTQTKGPSPASTKKRTTRTLPPRTPEAVDGRRHIDIQTDVYLEELTDTVPEADTSTQTD
AFLDRPPTPLFVPQKTGTDAITQIENGDLFDFDFEVEPILEVLVGKVLEQGLMEVLEEEEL
AAMRAHQEHFEQIRNAELVATQRMEAAERRKLEEKERRMQQERERVERERVVRQKVAASAF
ARGYLSGIVNTVFDRLVSSGYIYDPVMREVETAFMPWLKEQAIGYLARGVVARRVVDKLVE
DAAAALAANRSTLADKAASTAATVDAWAERQAKMEAELQGKELEAVRRRPTFVLRELKPAV
ASADAVEAAAAELTAQAEEAANAKWEADKAEAAEKARAEAEAAAEEQKALLEELAATAAAE
AEERGEEPPAEPPSLPDGVEPVDVEAEVAKAVEAVPKPPVKEVTDIDILSYMMDKGAITKD
AIIQALAVHALGDKAYTNHPAFAEAEGA

FIG. 2B

MVQAKAQQQLYTHAAEPKAVQQRRAKYREDETTQTLPTANIMFDRRVVRGNTYAARILPAD
ATQTQTKGPSPASTKKRTTRTLPPRTPEAVDGRRHIDIQTDVYLEELTDTVPEADTSTQTD
AFLDRPPTPLFVPQKTGTDAITQITDRQTDRQTGIENGDLFDFDFEVEPILEVLVGKVLE
QGLMEVLEEEELAAMRAHQEHFEQIRNAELVATQRMEAAERRKLEEKERRMQQERERVERE
RVVRQKVAASAFARGYLSGIVNTVFDRLVSSGYIYDPVMREVETAFMPWLKEQAIGYLARG
VVARRVVDKLVEDAAAALAANRSTLADKAASTAATVDAWAERQAKMEAELQGKELEAVRRR
PTFVLRELKPAVASADAVEAAAAELTAQAEEAANAKWEADKAEAAEKARAEAEAAAEEQKA
LLEELAATAAAEAEERGEEPPAEPPSLPDGVEPVDVEAEVAKAVEAVPKPPVKEVTDIDIL
SYMMDKGAITKDAIIQALAVHALGDKAYTNHPAFAEAEGA

```
                    SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
         (A) LENGTH: 10 amino acids
         (B) TYPE: amino acid
         (D) TOPOLOGY: linear (ii) MOLECULE TYPE: protein (v) FRAGMENT TYPE: internal (xi) SEQUENCE DESCRIPTION: SEQ ID NO:1:

Glu Gln Lys Leu Ile Ser Glu Glu Asp Leu
1               5                   10

(2) INFORMATION FOR SEQ ID NO:2:

(i) SEQUENCE CHARACTERISTICS:
         (A) LENGTH: 8 amino acids
         (B) TYPE: amino acid
         (D) TOPOLOGY: linear
```

(ii) MOLECULE TYPE: protein (v) FRAGMENT TYPE: internal (xi) SEQUENCE DESCRIPTION: SEQ ID NO:2:

Tyr Pro Tyr Pro Asp Val Tyr Ala
1               5

(2) INFORMATION FOR SEQ ID NO:3:

(i) SEQUENCE CHARACTERISTICS:
            (A) LENGTH: 8 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:3:

Asp Tyr Lys Asp Asp Asp Asp Lys
1               5

(2) INFORMATION FOR SEQ ID NO:4:

(i) SEQUENCE CHARACTERISTICS:
            (A) LENGTH: 12 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:4:

Lys Gly Phe Ser Tyr Phe Gly Glu Asp Leu Met Pro
1               5                   10

(2) INFORMATION FOR SEQ ID NO:5:

(i) SEQUENCE CHARACTERISTICS:
            (A) LENGTH: 1548 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

ATGGTGCAGG CTAAGGCGCA GCAGCAGCTG TACACGCACG CTGCAGAGCC GAAGGCAGTT        60

CAACAGCGGC GTGCCAAGTA TCGCGAGGAT GAGACGACGC AGACGCTGCC CACGGCAAAC       120

ATCATGTTCG ACCGTCGTGT AGTACGAGGC AACACATACG CCGCGCGCAT TCTGCCCGCC       180

GATGCCACGC AAACGCAAAC CAAGGGACCC TCGCCGGCAT CGACGAAGAA GAGGACAACA       240

CGGACGCTGC CGCCCCGGAC GCCGGAGGCC GTTGACGGCC GGCGGCACAT CGACATCCAA       300

ACGGACGTGT ATCTGGAGGA GCTGACAGAC ACCGTGCCGG AGGCTGACAC CTCCACGCAG       360

ACCGATGCCT TCCTGGACCG GCCCCCCACC CCGCTGTTTG TGCCGCAGAA GACGGGCACG       420

GACGCCATCA CCCAGATCGA GAACGGTGAC CTGTTTGACT TGACTTCGA GGTGGAGCCC       480

ATCCTGGAGG TGCTGGTGGG CAAGGTGCTG GAGCAGGGCC TGATGGAGGT GCTGGAGGAG       540

GAGGAGCTGG CGGCCATGCG CGCGCACCAG GAGCACTTCG AGCAGATTCG CAACGCCGAG       600

```
CTGGTGGCCA CACAGCGCAT GGAGGCGGCG GAGCGGCGCA AGCTGGAGGA GAAGGAGCGG    660

CGCATGCAGC AGGAGCGCGA GCGTGTCGAG CGCGAGCGCG TGGTGCGCCA GAAGGTGGCG    720

GCCAGCGCCT TTGCGCGCGG CTACCTGTCT GGCATTGTCA ACACGGTGTT TGACCGCTTG    780

GTGTCCAGCG GCTACATCTA CGACCCCGTC ATGCGCGAGG TGGAGACGGC GTTCATGCCC    840

TGGCTCAAGG AGCAGGCCAT CGGCTACCTG GCGCGCGGCG TGGTGGCGCG GCGCGTGGTG    900

GACAAGCTGG TGGAGGACGC GGCGGCGGCG CTGGCAGCCA ATCGCAGCAC CCTGGCGGAC    960

AAGGCCGCCA GCACGGCGGC CACGGTGGAC GCCTGGGCGG AGCGGCAGGC CAAGATGGAG   1020

GCGGAGCTGC AAGGCAAGGA GCTGGAGGCG GTGCGGCGGC GGCCCACGTT TGTGCTGCGC   1080

GAGCTCAAGC CCGCGGTGGC GAGCGCCGAT GCCGTCGAGG CGGCGGCCGC GGAGCTGACG   1140

GCGCAGGCGG AGGAGGCGGC CAACGCCAAG TGGGAGGCGG ACAAGGCGGA GGCGGCGGAG   1200

AAGGCGCGCG CCGAGGCGGA GGCGGCGGCG GAGGAGCAGA AGGCGCTGCT GGAGGAGTTG   1260

GCGGCCACGG CGGCGGCGGA GGCGGAGGAG CGCGGCGAGG AGCCGCCGGC GGAGCCGCCG   1320

TCGCTGCCGG ATGGCGTGGA GCCTGTGGAC GTGGAGGCTG AGGTGGCCAA GGCGGTGGAG   1380

GCTGTGCCCA AGCCGCCGGT CAAGGAGGTG ACAGACATTG ACATCCTGTC GTACATGATG   1440

GACAAGGGTG CCATCACCAA GGACGCCATC ATCCAGGCGC TGGCGGTGCA CGCGCTGGGC   1500

GACAAGGCCT ACACCAACCA CCCCGCGTTC GCCGAGGCGG AGGGCGCG              1548
```

(2) INFORMATION FOR SEQ ID NO:6:

(i) SEQUENCE CHARACTERISTICS:
        (A) LENGTH: 1581 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
ATGGTGCAGG CTAAGGCGCA GCAGCAGCTG TACACGCACG CTGCAGAGCC GAAGGCAGTT     60

CAACAGCGGC GTGCCAAGTA TCGCGAGGAT GAGACGACGC AGACGCTGCC CACGGCAAAC    120

ATCATGTTCG ACCGTCGTGT AGTACGAGGC AACACATACG CCGCGCGCAT TCTGCCCGCC    180

GATGCCACGC AAACGCAAAC CAAGGGACCC TCGCCGGCAT CGACGAAGAA GAGGACAACA    240

CGGACGCTGC CGCCCCGGAC GCCGGAGGCC GTTGACGGCC GGCGGCACAT CGACATCCAA    300

ACGGACGTGT ATCTGGAGGA GCTGACAGAC ACCGTGCCGG AGGCTGACAC CTCCACGCAG    360

ACCGATGCCT TCCTGGACCG GCCCCCCACC CCGCTGTTTG TGCCGCAGAA GACGGGCACG    420

GACGCCATCA CCCAGATCAC AGACAGACAG ACAGACAGAC AGACAGGGAT CGAGAACGGT    480

GACCTGTTTG ACTTTGACTT CGAGGTGGAG CCCATCCTGG AGGTGCTGGT GGGCAAGGTG    540

CTGGAGCAGG GCCTGATGGA GGTGCTGGAG GAGGAGGAGC TGGCGGCCAT GCGCGCGCAC    600

CAGGAGCACT TCGAGCAGAT TCGCAACGCC GAGCTGGTGG CCACACAGCG CATGGAGGCG    660

GCGGAGCGGC GCAAGCTGGA GGAGAAGGAG CGGCGCATGC AGCAGGAGCG CGAGCGTGTC    720

GAGCGCGAGC GCGTGGTGCG CCAGAAGGTG GCGGCCAGCG CCTTTGCGCG CGGCTACCTG    780

TCTGGCATTG TCAACACGGT GTTTGACCGC TTGGTGTCCA GCGGCTACAT CTACGACCCC    840

GTCATGCGCG AGGTGGAGAC GGCGTTCATG CCCTGGCTCA AGGAGCAGGC CATCGGCTAC    900

CTGGCGCGCG GCGTGGTGGC GCGGCGCGTG GTGGACAAGC TGGTGGAGGA CGCGGCGGCG    960
```

```
GCGCTGGCAG CCAATCGCAG CACCCTGGCG GACAAGGCCG CCAGCACGGC GGCCACGGTG    1020

GACGCCTGGG CGGAGCGGCA GGCCAAGATG GAGGCGGAGC TGCAAGGCAA GGAGCTGGAG    1080

GCGGTGCGGC GGCGGCCCAC GTTTGTGCTG CGCGAGCTCA AGCCCGCGGT GGCGAGCGCC    1140

GATGCCGTCG AGGCGGCGGC CGCGGAGCTG ACGGCGCAGG CGGAGGAGGC GGCCAACGCC    1200

AAGTGGGAGG CGGACAAGGC GGAGGCGGCG GAGAAGGCGC GCGCCGAGGC GGAGGCGGCG    1260

GCGGAGGAGC AGAAGGCGCT GCTGGAGGAG TTGGCGGCCA CGGCGGCGGC GGAGGCGGAG    1320

GAGCGCGGCG AGGAGCCGCC GGCGGAGCCG CCGTCGCTGC CGGATGGCGT GGAGCCTGTG    1380

GACGTGGAGG CTGAGGTGGC CAAGGCGGTG GAGGCTGTGC CCAAGCCGCC GGTCAAGGAG    1440

GTGACAGACA TTGACATCCT GTCGTACATG ATGGACAAGG GTGCCATCAC CAAGGACGCC    1500

ATCATCCAGG CGCTGGCGGT GCACGCGCTG GGCGACAAGG CCTACACCAA CCACCCCGCG    1560

TTCGCCGAGG CGGAGGGCGC G                                               1581
```

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

```
GATCACAGAC AGACAGACAG ACAGACAGAC AGGGATC                              37
```

(2) INFORMATION FOR SEQ ID NO:8:

(i) SEQUENCE CHARACTERISTICS:
        (A) LENGTH: 516 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Met Val Gln Ala Lys Ala Gln Gln Gln Leu Tyr Thr His Ala Ala Glu
 1               5                  10                  15

Pro Lys Ala Val Gln Gln Arg Arg Ala Lys Tyr Arg Glu Asp Glu Thr
                20                  25                  30

Thr Gln Thr Leu Pro Thr Ala Asn Ile Met Phe Asp Arg Val Val
         35                  40                  45

Arg Gly Asn Thr Tyr Ala Ala Arg Ile Leu Pro Ala Asp Ala Thr Gln
     50                  55                  60

Thr Gln Thr Lys Gly Pro Ser Pro Ala Ser Thr Lys Lys Arg Thr Thr
 65                  70                  75                  80

Arg Thr Leu Pro Pro Arg Thr Pro Glu Ala Val Asp Gly Arg His
                85                  90                  95

Ile Asp Ile Gln Thr Asp Val Tyr Leu Glu Glu Leu Thr Asp Thr Val
                100                 105                 110

Pro Glu Ala Asp Thr Ser Thr Gln Thr Asp Ala Phe Leu Asp Arg Pro
            115                 120                 125
```

```
Pro Thr Pro Leu Phe Val Pro Gln Lys Thr Gly Thr Asp Ala Ile Thr
130                 135                 140

Gln Ile Glu Asn Gly Asp Leu Phe Asp Phe Asp Phe Glu Val Glu Pro
145                 150                 155                 160

Ile Leu Glu Val Leu Val Gly Lys Val Leu Glu Gln Gly Leu Met Glu
            165                 170                 175

Val Leu Glu Glu Glu Glu Leu Ala Ala Met Arg Ala His Gln Glu His
            180                 185                 190

Phe Glu Gln Ile Arg Asn Ala Glu Leu Val Ala Thr Gln Arg Met Glu
            195                 200                 205

Ala Ala Glu Arg Arg Lys Leu Glu Glu Lys Glu Arg Arg Met Gln Gln
210                 215                 220

Glu Arg Glu Arg Val Glu Arg Glu Arg Val Val Arg Gln Lys Val Ala
225                 230                 235                 240

Ala Ser Ala Phe Ala Arg Gly Tyr Leu Ser Gly Ile Val Asn Thr Val
            245                 250                 255

Phe Asp Arg Leu Val Ser Ser Gly Tyr Ile Tyr Asp Pro Val Met Arg
            260                 265                 270

Glu Val Glu Thr Ala Phe Met Pro Trp Leu Lys Glu Gln Ala Ile Gly
            275                 280                 285

Tyr Leu Ala Arg Gly Val Val Ala Arg Arg Val Val Asp Lys Leu Val
            290                 295                 300

Glu Asp Ala Ala Ala Ala Leu Ala Ala Asn Arg Ser Thr Leu Ala Asp
305                 310                 315                 320

Lys Ala Ala Ser Thr Ala Ala Thr Val Asp Ala Trp Ala Glu Arg Gln
                325                 330                 335

Ala Lys Met Glu Ala Glu Leu Gln Gly Lys Glu Leu Glu Ala Val Arg
            340                 345                 350

Arg Arg Pro Thr Phe Val Leu Arg Glu Leu Lys Pro Ala Val Ala Ser
            355                 360                 365

Ala Asp Ala Val Glu Ala Ala Ala Glu Leu Thr Ala Gln Ala Glu
            370                 375                 380

Glu Ala Ala Asn Ala Lys Trp Glu Ala Asp Lys Ala Glu Ala Ala Glu
385                 390                 395                 400

Lys Ala Arg Ala Glu Ala Glu Ala Ala Glu Glu Gln Lys Ala Leu
                405                 410                 415

Leu Glu Glu Leu Ala Ala Thr Ala Ala Ala Glu Ala Glu Glu Arg Gly
            420                 425                 430

Glu Glu Pro Pro Ala Glu Pro Pro Ser Leu Pro Asp Gly Val Glu Pro
            435                 440                 445

Val Asp Val Glu Ala Glu Val Ala Lys Ala Val Glu Ala Val Pro Lys
450                 455                 460

Pro Pro Val Lys Glu Val Thr Asp Ile Asp Ile Leu Ser Tyr Met Met
465                 470                 475                 480

Asp Lys Gly Ala Ile Thr Lys Asp Ala Ile Ile Gln Ala Leu Ala Val
                485                 490                 495

His Ala Leu Gly Asp Lys Ala Tyr Thr Asn His Pro Ala Phe Ala Glu
            500                 505                 510

Ala Glu Gly Ala
515
```

(2) INFORMATION FOR SEQ ID NO:9:

(i) SEQUENCE CHARACTERISTICS:
(A) LENGTH: 527 amino acids (B) TYPE: amino acid
(D) TOPOLOGY: linear (ii) MOLECULE TYPE: protein (v) FRAGMENT TYPE: internal (xi) SEQUENCE DESCRIPTION: SEQ ID NO:9:

```
Met Val Gln Ala Lys Ala Gln Gln Leu Tyr Thr His Ala Ala Glu
1               5                   10                  15

Pro Lys Ala Val Gln Gln Arg Arg Ala Lys Tyr Arg Glu Asp Glu Thr
                20                  25                  30

Thr Gln Thr Leu Pro Thr Ala Asn Ile Met Phe Asp Arg Arg Val Val
                35                  40                  45

Arg Gly Asn Thr Tyr Ala Ala Arg Ile Leu Pro Ala Asp Ala Thr Gln
    50                  55                  60

Thr Gln Thr Lys Gly Pro Ser Pro Ala Ser Thr Lys Lys Arg Thr Thr
65                  70                  75                  80

Arg Thr Leu Pro Pro Arg Thr Pro Glu Ala Val Asp Gly Arg His
                    85                  90                  95

Ile Asp Ile Gln Thr Asp Val Tyr Leu Glu Glu Leu Thr Asp Thr Val
                100                 105                 110

Pro Glu Ala Asp Thr Ser Thr Gln Thr Asp Ala Phe Leu Asp Arg Pro
                115                 120                 125

Pro Thr Pro Leu Phe Val Pro Gln Lys Thr Gly Thr Asp Ala Ile Thr
130                 135                 140

Gln Ile Thr Asp Arg Gln Thr Asp Arg Gln Thr Gly Ile Glu Asn Gly
145                 150                 155                 160

Asp Leu Phe Asp Phe Asp Phe Glu Val Glu Pro Ile Leu Glu Val Leu
                165                 170                 175

Val Gly Lys Val Leu Glu Gln Gly Leu Met Glu Val Leu Glu Glu Glu
                180                 185                 190

Glu Leu Ala Ala Met Arg Ala His Gln Glu His Phe Glu Gln Ile Arg
                195                 200                 205

Asn Ala Glu Leu Val Ala Thr Gln Arg Met Glu Ala Ala Glu Arg Arg
210                 215                 220

Lys Leu Glu Glu Lys Glu Arg Arg Met Gln Gln Glu Arg Glu Arg Val
225                 230                 235                 240

Glu Arg Glu Arg Val Val Arg Gln Lys Val Ala Ala Ser Ala Phe Ala
                245                 250                 255

Arg Gly Tyr Leu Ser Gly Ile Val Asn Thr Val Phe Asp Arg Leu Val
                260                 265                 270

Ser Ser Gly Tyr Ile Tyr Asp Pro Val Met Arg Glu Val Glu Thr Ala
            275                 280                 285

Phe Met Pro Trp Leu Lys Glu Gln Ala Ile Gly Tyr Leu Ala Arg Gly
290                 295                 300

Val Val Ala Arg Arg Val Val Asp Lys Leu Val Glu Asp Ala Ala Ala
305                 310                 315                 320

Ala Leu Ala Ala Asn Arg Ser Thr Leu Ala Asp Lys Ala Ala Ser Thr
                325                 330                 335

Ala Ala Thr Val Asp Ala Trp Ala Glu Arg Gln Ala Lys Met Glu Ala
                340                 345                 350

Glu Leu Gln Gly Lys Glu Leu Glu Ala Val Arg Arg Pro Thr Phe
                355                 360                 365

Val Leu Arg Glu Leu Lys Pro Ala Val Ala Ser Ala Asp Ala Val Glu
370                 375                 380
```

```
Ala Ala Ala Ala Glu Leu Thr Ala Gln Ala Glu Glu Ala Ala Asn Ala
385                 390                 395                 400

Lys Trp Glu Ala Asp Lys Ala Glu Ala Ala Glu Lys Ala Arg Ala Glu
                405                 410                 415

Ala Glu Ala Ala Ala Glu Glu Gln Lys Ala Leu Leu Glu Glu Leu Ala
                420                 425                 430

Ala Thr Ala Ala Ala Ala Glu Ala Glu Arg Gly Glu Glu Pro Pro Ala
                435                 440                 445

Glu Pro Pro Ser Leu Pro Asp Gly Val Glu Pro Val Asp Val Glu Ala
                450                 455                 460

Glu Val Ala Lys Ala Val Glu Ala Val Pro Lys Pro Pro Val Lys Glu
465                 470                 475                 480

Val Thr Asp Ile Asp Ile Leu Ser Tyr Met Met Asp Lys Gly Ala Ile
                485                 490                 495

Thr Lys Asp Ala Ile Ile Gln Ala Leu Ala Val His Ala Leu Gly Asp
                500                 505                 510

Lys Ala Tyr Thr Asn His Pro Ala Phe Ala Glu Ala Glu Gly Ala
                515                 520                 525
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:10:

```
Pro His His Thr Thr Pro His His Thr Thr Pro His His Thr Thr
1               5                   10                  15
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

ACAGACAGAC AGACAGACAG ACAGACAG                                      28

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

GATCACAGAC AGACAGACAG ACAGACAGAC AGGGATC                                37

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:13:

Thr Asp Arg Gln Thr Asp Arg Gln Thr
1               5

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:14:

Gln Thr Asp Arg Gln Thr Asp Arg Gln
1               5

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:15:

Arg Gln Thr Asp Arg Gln Thr Asp
1               5

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:16:

Thr Asp Arg Gln Thr Asp
1               5

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:17:

Gln Thr Asp Arg Gln Thr
1               5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:18:

Arg Gln Thr Asp Arg Gln
1               5

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:19:

Gln Thr Asp Arg Gln
1               5

(2) INFORMATION FOR SEQ ID NO:20:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:20:

Thr Asp Arg Gln Thr
1               5

(2) INFORMATION FOR SEQ ID NO:21:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:21:

Asp Arg Gln Thr Asp
1               5

(2) INFORMATION FOR SEQ ID NO:22:

(i) SEQUENCE CHARACTERISTICS:

(A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:22:

Arg Gln Thr Asp Arg
1               5

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:23:

GTCCAGTCCA GTCCAGTCCA GTCCAGTCCA GTCCAGTCCA GTCCA                45

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:24:

Val Gln Ser Ser Pro
1               5

(2) INFORMATION FOR SEQ ID NO:25:

(i) SEQUENCE CHARACTERISTICS:
        (A) LENGTH: 11 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:25:

Val Gln Ser Ser Pro Val Gln Ser Ser Pro Val
1               5                   10

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:26:

```
Val Gln Ser Ser Pro Val Gln Ser Ser Pro Val Gln Ser Ser Pro
1               5                   10                  15
```

(2) INFORMATION FOR SEQ ID NO:27:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:27:

```
Ser Ser Pro Val Gln Ser Ser Pro Val Gln Ser Ser Pro Val
1               5                   10
```

(2) INFORMATION FOR SEQ ID NO:28:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:28:

```
Pro Val Gln Ser Ser Pro Val Gln Ser Ser Pro Val Gln Ser
1               5                   10
```

(2) INFORMATION FOR SEQ ID NO:29:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

```
TGGACTGGAC TGGACTGGAC TGGACTGGAC TGGACTGGAC TGGAC                45
```

(2) INFORMATION FOR SEQ ID NO:30:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:30:

```
Trp Thr Gly Leu Asp
1               5
```

(2) INFORMATION FOR SEQ ID NO:31:

(i) SEQUENCE CHARACTERISTICS:
        (A) LENGTH: 11 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:31:

Trp Thr Gly Leu Asp Trp Thr Gly Leu Asp Trp
1               5                   10

(2) INFORMATION FOR SEQ ID NO:32:

(i) SEQUENCE CHARACTERISTICS:
            (A) LENGTH: 15 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:32:

Trp Thr Gly Leu Asp Trp Thr Gly Leu Asp Trp Thr Gly Leu Asp
1               5                   10                  15

(2) INFORMATION FOR SEQ ID NO:33:

(i) SEQUENCE CHARACTERISTICS:
            (A) LENGTH: 14 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:33:

Gly Leu Asp Trp Thr Gly Leu Asp Trp Thr Gly Leu Asp Trp
1               5                   10

(2) INFORMATION FOR SEQ ID NO:34:

(i) SEQUENCE CHARACTERISTICS:
            (A) LENGTH: 14 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:34:

Asp Trp Thr Gly Leu Asp Trp Thr Gly Leu Asp Trp Thr Gly
1               5                   10

(2) INFORMATION FOR SEQ ID NO:35:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

ACGTACGTAC GTACGTACGT ACGTACGTAC GTACGT                          36

(2) INFORMATION FOR SEQ ID NO:36:

(i) SEQUENCE CHARACTERISTICS:
        (A) LENGTH: 4 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:36:

Thr Tyr Val Arg
1

(2) INFORMATION FOR SEQ ID NO:37:

(i) SEQUENCE CHARACTERISTICS:
        (A) LENGTH: 9 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:37:

Thr Tyr Val Arg Thr Tyr Val Arg Thr
1               5

(2) INFORMATION FOR SEQ ID NO:38:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:38:

Thr Tyr Val Arg Thr Tyr Val Arg Thr Tyr Val Arg
1               5                   10

(2) INFORMATION FOR SEQ ID NO:39:

(i) SEQUENCE CHARACTERISTICS:
        (A) LENGTH: 11 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:39:

Arg Thr Tyr Val Arg Thr Tyr Val Arg Thr Tyr
1               5                   10

(2) INFORMATION FOR SEQ ID NO:40:

(i) SEQUENCE CHARACTERISTICS:
        (A) LENGTH: 11 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:40:

Val Arg Thr Tyr Val Arg Thr Tyr Val Arg Thr
1               5                  10

(2) INFORMATION FOR SEQ ID NO:41:

(i) SEQUENCE CHARACTERISTICS:
         (A) LENGTH: 15 amino acids
         (B) TYPE: amino acid
         (D) TOPOLOGY: linear (ii) MOLECULE TYPE: protein (v) FRAGMENT TYPE: internal (xi) SEQUENCE DESCRIPTION: SEQ ID NO:41:

Pro His Leu Thr Ser Pro His Leu Thr Ser Pro His Leu Thr Ser
1               5                  10                  15

(2) INFORMATION FOR SEQ ID NO:42:

(i) SEQUENCE CHARACTERISTICS:
         (A) LENGTH: 91 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

GGATCCAAGA TCTGGTACCC CACACCACAC CACACCACAC CACACCACAC CACACCACAC        60

CACACCACAC CACACCACAA GATCTGAATT C                                       91

(2) INFORMATION FOR SEQ ID NO:43:

(i) SEQUENCE CHARACTERISTICS:
         (A) LENGTH: 26 amino acids
         (B) TYPE: amino acid
         (D) TOPOLOGY: linear (ii) MOLECULE TYPE: protein (v) FRAGMENT TYPE: internal (xi) SEQUENCE DESCRIPTION: SEQ ID NO:43:

Lys Ile Trp Tyr Pro Thr Pro His Thr Thr Pro His His Thr Thr
1               5                  10                  15

Pro His His Thr Thr Pro His His Lys Ile
             20                  25

(2) INFORMATION FOR SEQ ID NO:44:

(i) SEQUENCE CHARACTERISTICS:
         (A) LENGTH: 90 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:

```
GGATCCAGAT CTGGTACCCC TCACCTCACC TCACCTCACC TCACCTCACC TCACCTCACC        60

TCACCTCACC TCACCTCAAG ATCTGAATTC                                         90
```

(2) INFORMATION FOR SEQ ID NO:45:

(i) SEQUENCE CHARACTERISTICS:
        (A) LENGTH: 26 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:45:

```
Arg Ser Gly Thr Pro His Leu Thr Ser Pro His Leu Thr Ser Pro His
1               5                   10                  15

Leu Thr Ser Pro His Leu Thr Ser Arg Ser
            20                  25
```

(2) INFORMATION FOR SEQ ID NO:46:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

```
TGTGGTGTGG TGTGGTGTGG TGTGGTGTGG TGTGGTGTGG TGTGGTGTGG TGTGGTGTGG        60
```

(2) INFORMATION FOR SEQ ID NO:47:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:47:

```
CCACACCACA CCACACCACA CCACACCACA CCACACCACA CCACACCACA CCACACCACA        60
```

READING FRAME INDEPENDENT EPITOPE TAGGING

BACKGROUND OF THE INVENTION

1. Field of the Invention

This invention relates to epitope tagging, in particular, to improved epitope tags, the nucleotide sequences that encode them, methods for using the nucleotide sequences and tags, and resulting cellular and multicellular products.

2. Background Art

The publications and other reference materials referred to herein to describe the background of the invention and to provide additional detail regarding its practice are hereby incorporated by reference. For convenience, the reference materials are numerically referenced and grouped in the appended bibliography.

Epitope tagging is a recombinant DNA method for introducing immunoreactive peptides into the products of cloned genes (1–7). In particular, a DNA sequence encoding a sequence of amino acids that comprises a continuous epitope is inserted into the coding sequence of a cloned gene with the result that when the gene is expressed the protein of the gene is tagged with the epitope. The protein can then be detected and/or purified by virtue of its interaction with an antibody specific to the epitope. Epitope tags are typically 5–20 amino acids in length. Nucleotide sequences encoding the epitope are produced either by cloning appropriate portions of natural genes or by synthesizing a polynucleotide that encodes the epitope.

Epitope tagging is widely used for detecting, characterizing, and purifying proteins. The technique offers several advantages over alternative methods of detecting and purifying proteins. The small size of the epitope tag, which is usually 5–20 amino acids in length, generally has no effect on the biological function of the tagged protein. This contrasts with many larger fusion protein products, in which the activity or function of the fusion protein has been affected by the longer peptide label. Epitope tagging also offers tremendous time savings over the traditional method of producing an antibody to the specific protein being studied.

Epitope tagging involves adding a unique ëepitope tagí peptide sequence to the protein of interest by recombinant DNA techniques, creating a fusion protein. The resulting tagged protein can then be detected by and purified with an antibody specific for the epitope tag.

Epitope tagging methods have been used in a wide variety of applications, including western blot analysis, immunoprecipitation, immunofluorescence, and immunoaffinity purification of tagged proteins.

Epitope tagging was first described in 1984 by Munro and Pelham (1). A cDNA encoding the Drosophila melanogaster heat shock protein hsp70 was tagged at the 3' end of the coding sequence with a short oligonucleotide tag encoding either nine or fourteen amino acids of the peptide Substance P. After transfection of monkey COS cells, the tagged protein was detected using an anti-substance P monoclonal antibody. Since the initial report of Munro and Pelham, hundreds of investigations using epitope tagging have been reported in the scientific literature. Epitope tagging products and kits, which include various combinations of peptides, polynucleotides, and antibodies, are currently sold by a number of companies, including Boehringer-Mannheim, Indianapolis Ind.; Berkeley Antibody Company, Berkeley, Calif.; MBL International Corporation, Watertown, Mass.; Novagen, Madison Wis.; IBI, West Haven, Conn. and Life Technologies, Gaithersburg, Md.

To epitope tag a protein by conventional means, one begins with two DNA molecules: (1) a polynucleotide which is cloned in a plasmid vector and which includes a sequence of nucleotides encoding the protein as well as regulatory sequences (i.e. promoter, translations start, etc.) needed to express the protein; and (2) an oligonucleotide encoding the epitope with which the protein is to be tagged. The oligonucleotide is designed to encode, in one of its reading frames, an epitope recognized by a known antibody. One chooses a site in the polynucleotideís protein coding sequence for insertion of the oligonucleotide. The site may be at or near the 3' or the 5' end of the coding sequence, or somewhere in between the 3' and 5' ends. The insertion site for the oligonucleotide is typically a unique restriction site. The plasmid is linearized with the restriction endonuclease, and the oligonucleotide is ligated into the site. The tagged gene is then introduced into living cells. Epitope-tagged protein, which is subsequently expressed from the tagged gene, is detected and/or purified by immunochemical means.

Using conventional epitope tagging techniques, hundreds of different proteins have been epitope-tagged with numerous distinct peptides, including the ten amino aciid c-myc epitope (glu gln lys leu ile ser glu glu asp) derived from the human c-myc protein (8)); the nine amino acid HA-epitope (try pro try asp val try ala) (SEQ ID NO.2) derived from influenza virus hemagglutinin (9, 10), the eight amino acid FLAG epitope (asp try lys asp asp asp asp lys) (SEQ ID NO.3) derived from bacteriophage T7 (Castrucci et al., 1992. J. Virology 66:4647–4653) and the eleven amino acid epsilon-tag epitope (lys gly phe ser tyr phe gly glu asp leu met pro) (SEQ ID NO.4) derived from protein kinase C epsilon (Olah et al., 1994. Anal. Biochem. 221: 94–102). Indeed, there appears to be no practical limit to the number of possible epitope tags that can exist. Essentially any peptide can be used as an immunogen to raise antibodies that will recognize that same peptide when it is present within or at the termini of a protein (11, 12).

It is common practice in molecular biology to obtain antibodies that recognize the protein product of a cloned and sequenced gene by (1) synthesizing a peptide, typically ten to twenty amino acids in length, that corresponds to a portion of the protein, (2) immunizing an animal with the peptide, and (3) using the resulting antiserum to immunodetect or immunopurify the protein in which the peptide is situated. An example of this approach can be found in Sawin (15). A particularly relevant example can be found in Sugii et al. (13). Here, 23 overlapping peptides that cover the entire amino acid sequence of bovine conglutinin were synthesized and used individually as peptide epitopes to immunize rabbits. Every serum showed cross-reactivity with the complete conglutinin protein.

A problem with conventional epitope tagging involves a limited probability of successfully tagging the protein. Despite researchersí best efforts, not every insertion into a host polynucleotide of an oligonucleotide encoding an epitope tag is achieved in a reading frame which allows expression of the intended epitope. The probability of success using a conventional method depends, in part, on how much is known about the polynucleotide before the construction is commenced. If the nucleotide sequence is known, and if, therefore, the reading frame at the target restriction site is known, then an oligonucleotide with the epitope encoded in the correct reading frame can be chosen. In this case, the probability that a given insertion event will be the desired one is one in two for the reason that the orientation of the oligonucleotide with respect to the polynucleotide cannot be controlled by the experimenter, and only one of the two orientations will serve. If, on the other hand, the reading frame at the target restriction site is not known (as is frequently the case), then the probability of success drops to one in six because the reading frame will only be correct for one site out of three. The reading frame problem could be dealt with by using three different DNA fragments, each of which encodes the epitope tag in a different reading frame (16). However, that involves production of multiple constructs to assure finding the one of interest, which is an inefficient process.

Accordingly, for known epitope tagging procedures to be effective, the added DNA must be (1) in the appropriate orientation, and (2) in the correct reading frame. There are thus two obstacles inherent in conventional epitope tagging: an orientation obstacle and a reading frame obstacle.

The reading frame obstacle can only be avoided if the reading frame around the target restriction site is known. Otherwise, three different DNA fragments, each of which encodes the epitope tag in a different reading frame must be used. In particular, if the insertion into the coding sequence is at a random or arbitrarily selected site, e.g. at a unique restriction site, then for a given epitope-encoding oligonucleotide, the maximum likelihood that it is possible to successfully epitope-tag the gene product by insertion of the oligonucleotide at that site is only one in three (due to the reading frame obstacle). The experimenter is forced to isolate multiple insertions at the target site and test them individually in order to find the one of interest. The test may be arduous. For example, if the gene of interest is to be assayed in transgenic animals, it would be necessary to make numerous transgenic constructs and examine them individually.

In summary, when the reading frame of the target restriction site is not known, the likelihood that a particular insertion will successfully tag the protein is only one in six (due to the reading frame obstacle and the orientation obstacle). In other words, in five tries out of six the experimenter will fail, and in two cases out of three the experimenter is destined to fail.

DISCLOSURE OF THE INVENTION

The present invention overcomes the problem of inefficient epitope tagging. In one aspect, the present invention is directed to compositions of oligonucleotide sequences, and to methods of using them to more efficiently epitope tag proteins.

The invention is based on an oligonucleotide sequence comprising a repeating nucleotide sequence which encodes a repeating circularly permuted amino-acid sequence epitope. Regardless of the reading frame, the oligonucleotide sequence of the invention enables one to tag a protein with the same epitope from all three possible reading frames of the nucleotide sequence. This allows the present invention to overcome the inefficiency of epitope tagging caused by the reading frame obstacle, and, using certain embodiments of the invention, overcome the orientation obstacle as well.

The invention is directed to:

1. Oligonucleotides. A major aspect of the invention is directed to an oligonucleotide which comprises a nucleotide sequence that encodes an epitope. The nucleotide sequence encodes the epitope independently of the reading frame of the nucleotide sequence. The oligonucleotide is adapted for insertion into a target nucleotide sequence and for expression in a host cell. In a preferred embodiment, the nucleotide sequence encoding the epitope is a repeating sequence which has the formula (S)n wherein S is a sequence of nucleotides whose number is not evenly divisible by 3, and n is an integer equal to or greater than the number of nucleotides in S. Such an oligonucleotide is here defined as a "universal oligonucleotide." The claimed oligonucleotide sequences do not include those which upon insertion into the target sequence encode a stop codon in any reading frame. A version of the claimed oligonucleotide has sequences that flank the repeating nucleotide sequence and which allow insertion of the oligonucleotide into the target sequence such that the reading frame encoded by the target nucleotide sequence is not broken downstream of the oligonucleotide when the oligonucleotide is inserted in said target nucleotide sequence.

2. DNA Constructs. The invention includes a DNA construct which comprises a nucleotide sequence which codes for an epitope independently of the reading frame of said nucleotide sequence. In one aspect, the DNA construct, codes for a fusion polypeptide, which comprises a native polypeptide fused to the epitope. When expressed, the fusion polypeptide is distinguishable from the native polypeptide by the absence of the ability of the native polypeptide to specifically bind to an antibody or other reagent specific for the universal epitope or by the absence of the native polypeptide to display the antigenicity of the universal epitope.

3. Vectors. Another aspect of the invention is a vector which comprises the DNA construct of the invention incorporated into a plasmid that is capable of stably transforming host cells. The vector can be incorporated into a virus or a transposon capable of transforming host cells.

4. Probes. The invention is further directed to probes which have a nucleotide sequence sufficiently complementary to a nucleotide sequence which codes for an epitope independently of the reading frame of said nucleotide sequence.

5. Epitopes. Another aspect of the invention is directed to an epitope which comprises a sequence of amino acids which is encoded by a nucleotide sequence independently of the reading frame of the nucleotide sequence. The nucleotide sequence has the formula $(S)_n$ wherein S is a sequence of nucleotides whose number is not evenly divisible by 3, and n is an integer equal to or greater than the number of nucleotides in S. Such an epitope is here defined as a "universal epitope".

6. Fusion Polypeptides. In a further aspect of the invention, a fusion polypeptide is claimed. A fusion polypeptide of the invention comprises a native protein that comprises a universal epitope which is reactive with an antibody or other reagent specific for the universal epitope. The epitope comprises a sequence of amino acids encoded by the universal oligonucleotide of the invention. That is to say, the oliognucleotide comprises a nucleotide sequence adapted for insertion into a target nucleotide sequence and for expression in a host cell, the nucleotide sequence encoding the epitope independently of the reading frame of said nucleotide sequence.

7. Transformed Cellular and Multicellular Products. In yet another aspect, the invention provides either a host cell, an animal, or a plant transformed with one of the vectors of the invention.

8. Antibodies, Hybridomas, and Methods for Making. An additional feature of the invention is directed to antibodies that are specific for an epitope encoded by a nucleotide sequence independently of the reading frame of said nucleotide sequence. The antibodies are further reactive with immunologically reactive fusion polypeptides comprising the epitope, and fragments thereof comprising the epitope. The antibodies of the invention may be polyclonal or monoclonal.

Yet another aspect of the invention is a hybridoma or immortalized cell line which secretes monoclonal antibodies specific for an epitope which is encoded by a nucleotide sequence independently of the reading frame of said nucleotide sequence.

Methods for producing the polyclonal or monoclonal antibodies of the invention are provided by the invention. The method for producing polyclonal antibodies specific for an epitope encoded by a nucleotide sequence independently of the reading frame of said nucleotide sequence involves administering a sufficient amount of an antigen comprising said epitope to an animal and after a sufficient period of time collecting said polyclonal antibodies from said animal. The method for producing monoclonal antibodies specific for an epitope encoded by a nucleotide sequence independently of the reading frame of said nucleotide sequence comprises culturing a hybridoma or immortalized cell line of the invention and recovering the monoclonal antibodies.

9. Other Reagents Specific to Universal Epitopes, and Methods for Making An additional feature of the invention is directed to non-antibody reagents that bind specifically to universal epitopes. A number of methods, often called combinatorial methods, are known in the art to identify such reagents. Peptide reagents can be identified and produced, for example, using phage display (17, 18), random peptide display in bacteria (19, 20), or Selectide approaches (20, 21). DNA or RNA molecules can be identified and produced, for example, using the SELEX approach (22, 23).

10. Methods for Epitope Tagging and Production of Fusion Proteins. The invention is also directed to a method for epitope tagging a native polypeptide to produce a fusion protein or polypeptide. The method involves attaching an oligonucleotide to the coding sequence of a native polypeptide to produce a tagged gene coding for a fusion polypeptide which comprises an epitope, which is coded for by the oligonucleotide, which itself comprises a nucleotide sequence which encodes the epitope independently of the reading frame of said nucleotide sequence. A further step of the method introduces the tagged gene into an expression system under conditions sufficient for transcription of the tagged gene to yield mRNA, and conditions sufficient for the mRNA to be translated to yield the fusion polypeptide. The fusion polypeptide is distinguishable from the native polypeptide by the absence of antigenicity of the native polypeptide to an antibody specific for the epitope.

The invention is also directed to another method of epitope tagging which involves by a single event tagging genes, transcripts and proteins in a eukaryotic cell. This method comprises a step of introducing into an intron within a gene a DNA sequence including a first nucleotide sequence, an acceptor site for RNA splicing, a second nucleotide sequence, and a donor site for RNA splicing. The first nucleotide sequence is necessary for splice acceptor function. The second nucleotide sequence encodes an epitope recognized by an antibody, other reagent or molecule. A further step promotes expression of the gene in a eukaryotic cell to produce a protein product, which comprises a peptide epitope encoded by the second nucleotide sequence as part of its primary structure. A unique aspect of the invention is directed to the second nucleotide sequence, which encodes an epitope independently of the reading frame of the second nucleotide sequence.

11. Method for Purifying a Polypeptide. Another aspect of the invention is directed to a method for purifying a polypeptide. This method involves tagging a target sequence which encodes a polypeptide with a nucleotide sequence which encodes an epitope independent of the reading frame of the nucleotide sequence to produce a tagged target sequence which encodes a fusion polypeptide. The tagged target sequence is expressed in an expression system to produce the fusion polypeptide, which is then purified.

12. Method to Detect a Polypeptide. The invention is directed to method for detecting a polypeptide. A first step of this method involves tagging a target sequence which encodes a polypeptide with a nucleotide sequence which encodes an epitope independent of the reading frame of the nucleotide sequence to produce a tagged target sequence which encodes a fusion polypeptide. It is understood that the fusion polypeptide comprises a universal epitope of the invention. The tagged target sequence is then expressed in an expression system to produce said fusion polypeptide. The expression system is then contacted with a sufficient amount of an antibody or reagent which is specific for the epitope under conditions which produce a detectable signal that indicates a reaction between the fusion polypeptide and antibody or reagent, thereby indicating the presence of the polypeptide of interest.

13. Kits for Epitope Tagging. A kit for epitope tagging is provided by the invention. The kit comprises antibodies or other reagents specific for the epitope or fusion specific for a fusion protein comprising the epitope. Further embodiments of the kit additionally comprise an oligonucleotide or DNA construct which comprises a nucleotide sequence which encodes an epitope and which is adapted for insertion into a target nucleotide sequence and for expression in a host cell. The nucleotide sequence encodes the epitope independently of the reading frame of the nucleotide sequence. Other embodiments of the kit are directed to additional elements such as probes sufficiently complementary to a nucleotide sequence which codes for the epitope. One embodiment of the kit comprises a DNA construct which codes for a fusion polypeptide which comprises a native polypeptide fused to the epitope. Still another version of the kit comprises a vector suitable for incorporating the DNA construct.

It is an object of the present invention that the claimed oligonucleotides, epitopes, fusion proteins, DNA constructs, vectors, probes, antibodies, transformed cellular and multicellular organisms, and methods for making and using them provide a set of robust tools which are more efficient than existing ones for analyzing and dissecting complex biological processes and systems. The present invention achieves this object in part by discovering new genes, determining the size and abundance of proteins produced by newly discovered genes, tracking the movement of proteins within cell membranes, monitoring receptor binding and internalization of exogenous proteins, identifying the components of functional protein complexes, purifying proteins, discovering the function of proteins, and in particular, proteins that are unstable, are difficult to purify, or share epitopes with a number of other proteins.

The above-discussed and many other features and attendant advantages of the present invention will become better understood by reference to the following detailed description of the invention taken in conjunction with the accompanying drawings.

BRIEF DESCRIPTION OF THE DRAWINGS

FIGS. 1(a) (SEQ ID NO.5 and (b) (SEQ ID NO.6) show the coding sequence encoding the Chlamydomonoas protein RSP3 before (a) and after (b) the insertion of the 37-mer oligonucleotide GAT CAC AGA CAG ACA GAC AGA CAG ACA GAC AGG GAT C (SEQ ID NO.7).

FIGS. 2(a) (SEQ ID NO.8) and (b) (SEQ ID NO.9) show the untagged and tagged amino acid sequence of the RSP3 protein encoded by the coding sequences shown, respectively, in FIGS. 1(a) and (b).

MODES OF CARRYING OUT THE INVENTION

General Description and Definitions

Figure 3A:
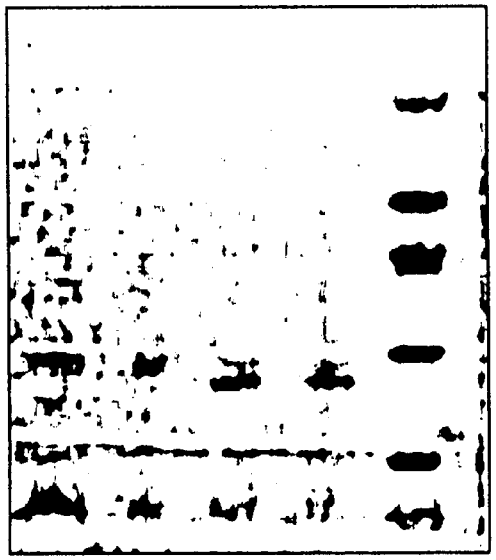
FIGS. 3A and 3B shows the reactivity of a monoclonal antibody made against the peptide (PHHTT)$_3$ to a GST fusion protein containing the (PHHTT)$_3$ sequence.
Figure 3B:
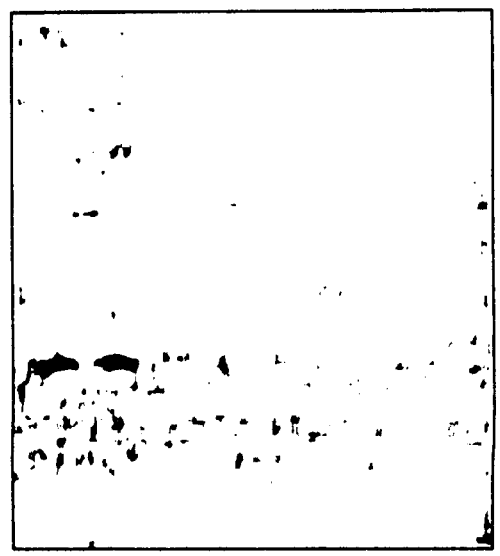

The practice of the present invention will employ, unless otherwise indicated, conventional biochemistry, immunology, molecular biology and recombinant DNA techniques within the skill of the art. Such techniques are explained fully in the literature. See, e.g. Maniatis et al., Molecular Cloning: A Laboratory Manual (1982); DNA Cloning: A Practical Approach, vol., I & II (D. Glover, ed.); Oligonucleotide Synthesis (N. Gait, ed., 1984); Nucleic Acid Hybridization (B. Hames and S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984); Peptide Antigens, A Practical Approach, ed. G. B. Wisdom (1994), Oxford University Press, New York, N.Y.; and immunological Recognition of Peptides in Medicine and Biology, eds. N. D. Zegers, W. J. A. Boersma, and E. Claassen (1995), CRC Press, Boca Raton, Fla.; Molecular Biology and Biotechnology, (ed. Robert A. Meyers, 1995) VCH Publishers, New York, N.Y.

The following terminology will be used in accordance with the definitions set out below in describing the present invention.

As used herein, the term "epitope" means that portion of a recombinant or non-recombinant protein that is recognized by a particular antibody species or recognized by another molecule that interacts specifically with the protein.

The term "expression system" is well understood in the art to mean either an in vitro system or cellular or multicellular organism capable of transcribing and translating nucleotide sequences to produce polypeptides.

As used herein, the term "tagging" or "tagging a target sequence" refers to introducing by recombinant methods one or more nucleotide sequences encoding a peptide epitope into a polypeptide-encoding gene, i.e. a target sequence so that the gene expresses a fusion polypeptide which comprises the peptide epitope.

The term "fusion polypeptide" or "fusion protein" refers to a polypeptide which has been tagged with a peptide epitope. The amino acid sequence of the fusion protein comprises the peptide epitope amino acid sequence, which epitope may be a universal epitope if it was encoded by a nucleotide sequence which encodes the peptide epitope independently of the reading frame of the nucleotide sequence.

The twenty amino acids with abbreviations and messenger RNA code designations are as follows:

| | | | |
|---|---|---|---|
| TTT phe F | TCT ser S | TAT tyr Y | TGT cys C |
| TTC phe F | TCC ser S | TAC tyr Y | TGC cys C |
| TTA leu L | TCA ser S | TAA OCH Z | TGA OPA Z |
| TTG leu L | TCG ser S | TAG AMB Z | TGG trp W |
| CTT leu L | CCT pro P | CAT his H | CGT arg R |
| CTC leu L | CCC pro P | CAC his H | CGC arg R |
| CTA leu L | CCA pro P | CAA gln Q | CGA arg R |
| CTG leu L | CCG pro P | CAG gln Q | CGG arg R |
| ATT ile I | ACT thr T | AAT asn N | AGT ser S |
| ATC ile I | ACC thr T | AAC asn N | AGC ser S |
| ATA ile I | ACA thr T | AAA lys K | AGA arg R |
| ATG met M | ACG thr T | AAG lys K | AGG arg R |
| GTT val V | GCT ala A | GAT asp D | GGT gly G |
| GTC val V | GCC ala A | GAC asp D | GGC gly G |
| GTA val V | GCA ala A | GAA glu E | GGA gly G |
| GTG val V | GCG ala A | GAG glu E | GGG gly G |

The present invention overcomes the previously mentioned "reading frame obstacle" by providing a DNA construct for epitope-tagging irrespective of reading frame, which makes the construction of appropriately tagged genes three times more efficient as is otherwise possible with conventional methods of epitope tagging. In other words, a single DNA construct within the scope of the present invention enables one to tag a protein with the same epitope from all three possible reading frames of the nucleotide sequence encoding the epitope.

The invention provides an oligonucleotide which comprises a nucleotide sequence that encodes an epitope. The nucleotide sequence encodes the epitope independently of the reading frame of the nucleotide sequence. The oligonucleotide is adapted for insertion into a target nucleotide sequence, and is also adapted for expression in a host cell.

The oligonucleotide of the invention comprises a nucleotide sequence of the form $(S)_n$ where S is a sequence of nucleotides whose number is not evenly divisible by 3 and n is an integer equal to or greater than the number of nucleotides in S. The sequence S is chosen such that any oliognucleotide having sequence $(S)_n$ does not includes stop codons. In practice, the oligonucleotide is inserted into the coding sequence of a cloned gene in such a way that the reading frame 3' to the inserted oligonucleotide is maintained and the gene is expressed when inserted into living host cells. As a result, an epitope-tagged (i.e. peptide-tagged) protein is produced in the cell.

A peptide epitope is encoded in each of the three reading frames of the oligonucleotide $(S)_n$ (here defined as Peptide 1, Peptide 2, and Peptide 3) and is known from the sequence of codons inherent in the three reading frames of the linear sequence of nucleotides in the oligonucleotide $(S)_n$. These peptides are related to one another by a simple circular permutation of the same peptide, whose length is the same number as the number of nucleotides in S. In a method of the invention, that same peptide is used to immunize an animal in order to make polyclonal or monoclonal antibodies specific for that same peptide, and specific for the related, circularly permuted peptide epitopes. In that manner, an antibody specific to a peptide that is common to Peptides 1, 2, and 3 is chosen. That antibody is used to immunolocalize and/or immunopurify the epitope-tagged (i.e. peptide-tagged) protein present in, or derived from, the living host cells in which the tagged gene is expressed.

For example, take the case where S is 4 and n is 7 for the sequence ACAG. In this case, the oligonucleotide of the invention comprises the nucleotide sequence (ACAG)7 (SEQ ID NO.11), i.e. a 7-repeat of the sequence ACAG or ACAGACAGACAGACAGACAGACAGACAG. The invention provides adaptations to the oligonucleotide which allow it to be inserted into a target sequence and which adapt the nucleotide sequence for expression in a host cell as follows: An oligonucleotide is synthesized consisting of the (ACAG)7 (SEQ ID NO.11) sequence surrounded by one or more flanking sequences such as a few additional nucleotides that provide flanking restriction sites and that assure that the oligonucleotide will not break the reading frame when inserted into a corresponding restriction site in the target gene (i.e. assuring that the insert in the gene will be 3N nucleotides in length). An example is a 37-mer GATCACAGACAGACAGACAGACAGACAGACAGGGATC (SEQ ID NO.12) that contains the (ACAG)7 (SEQ ID NO.11) sequence flanked or surrounded by MboI (GATC) sites and a G at position 33.

The 37-mer oligonucleotide is inserted into an MboI site within the coding sequence of a cloned gene or cDNA. For example, the target could be a cDNA including the coding sequence encoding the Chlamydomonoas protein RSP3 (25) shown in FIG. 1(*a*). This sequence contains a single MboI site, shown in bold type in the figure. When the 37-mer is inserted at the MboI site, the result is the sequence shown in FIG. 1(*b*). The tagged gene is then introduced into living cells using the DNA constructs or DNA vectors of the invention. The amino acid sequences of an untagged and tagged RSP3 protein are shown, respectively, in FIGS. 2(*a*) and (*b*).

Hypothetical translation of the (ACAG)$_7$ (SEQ ID NO.11) sequence in reading frame 0 (i.e. beginning with the first nucleotide) yields the amino acid sequence asp arg gln thr asp arg gln thr (SEQ ID NO.13). In reading frame 1 (beginning with the second nucleotide), it yields the sequence gln thr asp arg gln thr asp arg gln (SEQ ID NO.14. In reading frame 2 (beginning with the third nucleotide) it yields the sequence arg gln thr asp arg gln thr asp (SEQ ID NO.15). It will be understood that the epitope of the invention can be any one of the repeating amino-acid sequences encoded independently of the reading frame of the sequence (S)$_n$, which here is (4)$_7$, and in particular (ACAG)$_7$ (SEQ ID NO.11). Each of these amino acid sequences is related to the other sequences by a circular permutation of a repeating tetrapeptide. Three circularly permuted hexapeptides are common to all three sequences: thr asp arg gln thr (SEQ ID NO.16), gln, thr asp arg gln thr (SEQ ID NO.17, and arg gln thr asp arg gln (SEQ ID NO.18), any of which is an epitope of the invention. Likewise, the pentapeptides gln thr asp arg gln (SEQ ID NO.19), thr asp arg gln thr (SEQ ID NO.20), asp arg gln thr asp (SEQ ID NO.21), and arg gln thr asp arg (SEQ ID NO.22), are all epitopes of the invention. According to the method of the invention for producing antibodies (polyclonal or monclonal), one of the circularly permuted peptides is chosen, and is used as an immunogen for injecting an animal to produce an antibody recognizing the peptide. For example a mouse monoclonal recognizing gln thr asp arg gln thr (SEQ ID NO.17) is produced. Techniques within the skill of the art of immunology for making polyclonal and monoclonal antibodies are explained filly in the literature. See Current Protocols in Immunology, eds. Coligan et al., John Wiley and Sons, publ. (1996); Antibodies, A Laboratory Manual, Harlow and Lane, Cold Spring Harbor Laboratory Press (1988), and reference number 14. For example, proteins from the cells containing the tagged gene are separated by SDS gel electrophoresis. The proteins are transferred to nitrocellulose and probed with antibody. Epitope-tagged protein is visualized using alkaline phosphatase-conjugated anti-mouse IgG secondary antibody.

It is important to emphasize that the repeating oligonucleotide sequences and peptide sequences of the invention constitute only a miniscule fraction of all possible oligonucleotides or peptides of equal size. For example, when S equals 4 nucleotides and n equals 15 (giving a sixty-nucleotide oligonucleotide and a twenty amino-acid peptide), there are exactly 208 sequences of the invention (DNA or protein) possible. The number 208 is arrived at as follows. There can exist 256 ($4^4$) repeating four-nucleotide sequences. Of these 48 include nonsense codons. (The number 48 is arrived at by summing the fraction of nonsense codons (3/64) over the four repeating codons in the oligonucleotide and multiplying by 256.) 48 is subtracted from 256 to give 208. Similarly when S equals 5 nucleotides and n equals 12, there are exactly 1024−240=784 sequence of the invention. In dramatic contrast, the number of possible sixty-nucleotide sequences equals $4^{60}$, and the number of possible twenty amino acid peptides is $20^{20}$. Both of these numbers are truly astronomical—making it is extremely unlikely that any of the oligonucleotides or peptides of the invention even exist in the natural world.

In a further elaboration of the invention, the choice of an oligonucleotide of the form (S)$_n$ is restricted to those cases where the oligonucleotide sequence, in the antisense orientation, also lacks nonsense codons. All such antisense oligonucleotides, like all sense oligonucleotides, encode in each reading frame peptide epitopes that are related to each other by a simple circular permutation of a repeating peptide sequence. Two antibodies of the invention—one to a peptide epitope present in each "forward peptide" and one to a peptide epitope present in each "reverse peptide" are used to detect and/or purify the tagged protein. Here both the reading frame obstacle and the orientation obstacle are overcome, and so the probability of successful epitope tagging is fully 100%. An example is the sequence (GTCCA)$_9$ (SEQ ID NO.23), which encodes the repeating pentapeptide val gln ser ser pro (SEQ ID NO.24). In its three reading frames, the sequence encodes the three related peptides shown below. One of the several common peptides (val gln ser ser pro val val gln ser ser pro val (SEQ ID NO.25) encoded in each reading frame is underlined.

```
GTC CAG TCC AGT CCA GTC-        (SEQ ID NO.23)
    CAG TCC AGT CCA GTC CAG TC-
                            C AGT CCA

V   Q   S   S   P   V   Q   S   S   P   V   Q   S   S   P

S   S   P
V   Q   S   S   P   V   Q   S   S   P   V

P
V   Q   S   S   P   V   Q   S   S   P   V   Q   S
```

In the reverse orientation, the sequence is (TGGAC)$_9$ (SEQ ID NO.29) which encodes the repeating pentapeptide trp thr gly leu asp (SEQ ID NO.30). In its three reading frames, the sequence encodes the three related peptides shown below. One of the several common peptides (trp thr gly leu asp trp thr gly leu asp (SEQ ID NO.25) encoded in each reading frame is underlined.

```
TGG ACT GGA CTG GAC TGG ACT GGA CTG GAC TGG ACT GGA CTG GAC  (SEQ ID NO.29)

W   T   G   L   D   W   T   G   L   D   W   T   G   L   D

G   L   D   W   T   G   L   D   W   T   G   L   D   W

D   W   T   G   L   D   W   T   G   L   D   W   T   G
```

Using two antibodies or other reagents, one recognizing the sequence val gln ser ser pro val gln ser ser pro (SEQ ID NO.25) and one the sequence trp thr gly leu asp trp thr gly leu asp trp (SEQ ID NO.31), the protein encoded by a gene tagged with the sequence is recognized irrespective of the reading frame or orientation of the inserted oligonucleotide. Accordingly, the oligonucleotide of the invention includes those nucleotide sequences that also encode a second amino acid sequence epitope on the antisense strand.

In some cases the universal oligonucleotide is palindromic and so the forward and reverse oligonucleotides are the same, as are the forward and reverse peptides. In these cases the protein encoded by a gene tagged with the sequence is recognized by a single antibody or other specific reagent irrespective of the reading frame or orientation of the inserted oligonucleotide.

An example is the palindromic sequence (ACGT)$_9$ (SEQ ID NO.35), which encodes the repeating tetrapeptide thr tyr val arg (SEQ ID NO.36). In its three reading frames, the sequence encodes the three related peptides (thr tyr val arg thr tyr val arg try (SEQ ID NO.37) shown below, in which one of the several common peptides is underlined.

```
ACG TAC GTA CGT ACG TAC GTA CGT ACG TAC GTA CGT  (SEQ ID NO.35)

T   Y   V   R   T   Y   V   R   T   Y   V   R

R   T   Y   V   R   T   Y   V   R   T   Y

V   R   T   Y   V   R   T   Y   V   R   T
```

Because the oligonucleotide sequence is palindromic, it encodes the identical peptide in reverse orientation. Using a single antibody or other specific reagent recognizing the sequence thr try val arg thr tyr val arg try (SEQ ID NO.37), the protein encoded by a gene tagged with the sequence is recognized irrespective of the reading frame or orientation of the inserted oligonucleotide.

The scope of the present can be, in part, illustrated by a list of peptide epitopes of the invention which would result from translation of an oligonucleotide of the invention comprising repeating four-nucleotide sequences, i.e., S=4 nucleotides, inserted in the sense strand of a target sequence. Generation of such a list is explained in the specification above.

In order that the invention described herein may be more fully understood, the following examples are set forth. It should be understood that these examples are for illustrative purposes only and are not to be construed as limiting the scope of this invention in any manner.

EXAMPLE 1

1. Generation of Polyclonal Mouse Sera Against the Peptide (pro his his thr thr)$_3$ (SEQ ID NO.10)

A Multiple Antigen Peptide (MAP) carrying the sequence (pro his his thr thr)$_3$ (SEQ ID NO.10) was synthesized using standard procedures (Tam and Shao. 1993. Current Protocols in Immunology, Suppl. 7: 9.6.1–9.6.18). A 1 mg/ml solution of the peptide in 0.1M Sodium Bicarbonate was prepared and stored at −80 degrees C. Mice were immunized with 100 micrograms of the peptide in Freund's complete adjuvant and boosted with 100 micrograms of the peptide in Freund's incomplete adjuvant on days 21, 49 and 77 post-immunization and bled on day 82. Subsequent boosts were given two to three weeks after the first bleed, and blood samples were taken five days after each boost. Sera were prepared from whole blood by standard methods and immunoreactivity against the immunogen was assayed by ELISA in 96 well plates using standard methods. The blank values in the assay were 0.13 per well. The data, examples of which are shown in Table 1 below, demonstrated distinct immunoreaction to the (pro his his thr thr)$_3$ (SEQ ID NO.10) peptide by all four mice that were immunized.

TABLE 1

Immunoreactivity of mouse sera to the (prohisthrthr)$_3$(SEQ ID NO.10) immunogen.

| | Serum - bleed at day 112 | | Serum - bleed at day 80 | |
| --- | --- | --- | --- | --- |
| | 1:1000 | 1:2000 | 1:1000 | 1:2000 |
| Mouse 1 | 3.00 | 2.14 | 0.94 | 0.26 |
| Mouse 2 | 2.43 | 0.99 | 1.24 | 0.34 |
| Mouse 3 | 2.05 | 0.70 | 1.72 | 0.55 |
| Mouse 4 | 2.98 | 2.74 | 1.68 | 0.37 |

2. Generation of Polyclonal Mouse Sera Against the Peptide (pro his leu thr ser)$_3$ (SEQ ID NO.41)

A Multiple Antigen Peptide (MAP) carrying the sequence (pro his leu thr ser)$_3$ (SEQ ID NO.41) was synthesized using standard procedures (Tam and Shao. 1993. Current Protocols in Immunology, Suppl. 7: 9.6.1–9.6.18). A 1 mg/ml solution of the peptide in 0.1M Sodium Bicarbonate was prepared and stored at −80 degrees C. Mice were immunized with 100 micrograms of the peptide in Freund's complete adjuvant and boosted with 100 micrograms of the peptide in Freund's incomplete adjuvant on days 21, 49 and 77 post-immunization and bled on day 82. Subsequent boosts were given two to three weeks after the first bleed, and blood samples were taken five days after each boost. Sera were prepared from whole blood by standard methods and immunoreactivity against the immunogen was assayed by ELISA in 96 well plates using standard methods. Representative data are shown in Table 2 below. The blank values in the assay were 0.13 per well. Although the (pro his leu thr ser)$_3$ (SEQ ID NO.41) peptide was less immunogenic than the (pro his leu thr ser)$_3$ (SEQ ID NO.41) peptide, distinct immunoreaction to the (PHLTS)$_3$ peptide was observed for each of the five mice that were immunized.

TABLE 2

Immunoreactivity of mouse sera to the (prohisleuthrser)$_3$(SEQ ID NO.41) immunogen.

|  | Serum - bleed at day 112 | | Serum - bleed at day 80 | |
| --- | --- | --- | --- | --- |
|  | 1:250 | 1:500 | 1:250 | 1:500 |
| Mouse 1 | 0.42 | 0.20 | 0.35 | 0.16 |
| Mouse 2 | 1.11 | 0.66 | 0.68 | 0.29 |
| Mouse 3 | 1.39 | 0.81 | 0.65 | 0.28 |
| Mouse 4 | 1.94 | 1.18 | 1.56 | 0.91 |
| Mouse 5 | 1.23 | 0.81 | 0.47 | 0.24 |

3. Generation of Monoclonal Antibodies Against the (pro his his thr thr)$_3$ (SEQ ID NO.10) Peptide.

A splenectomy were performed on mouse 4 of Table 1, and hybridomas were generated and cultured using standard methods (Antibodies, A Laboratory Manual, 1988. Harlow and Lane, Cold Spring Harbor Laboratory Press (1988). Five clones secreting reactive immunoglobulins were identified and cultured.

4. Production, Detection, and Analysis of Immunoreactive GST-Fusion Proteins Expressing the (pro his his thr thr)$_3$ (SEQ ID NO.10) and (pro his his thr thr)$_3$ (SEQ ID NO.10) peptides.

To test reactivity of antisera to proteins which were epitope tagged according to the method of the invention, GST (glutathione-S-transferase) fusion proteins containing the (pro his his thr thr)$_3$ (SEQ ID NO.10) and (pro his his thr thr)$_3$ (SEQ ID NO.10) peptides were prepared as follows.

To produce a fusion polypeptide with a (pro his his thr thr)$_3$ (SEQ ID NO.10) tag, a DNA oligonucleotide of the invention was produced which had the 91 nucleotide sequence:

```
GGATCCAAGATCTGGTACCCCACACCACACCACACCACACCA (SEQ ID NO.42)
CACCACACCACACCACACCACACCACACCACACCACAAGATCTGAATTC
```

It was synthesized by standard methods, cut with the restriction enzymes BamI and EcoRI, and cloned into the vector pGEX-2T (Pharmacia, Piscataway, N.J.) that had been cut with the same two enzymes, thus producing a vector of the invention. The tagged vector was transformed into E. coli DH5 alpha cells and transformants, i.e host cells transformed by the vector were analyzed by standard methods to confirm that they contained the expected recombinant plasmid. Based on the known sequence of the pGEX-2T plasmid (Smith and Johnson. 1988. Gene 67:31–40) it was expected that the insert into the target GST gene would lead to the introduction of the peptide lys ile trp tyr pro thr pro his his thr thr pro his his thr thr pro his his thr thr pro his his lys ile (SEQ ID NO.43) within the GST protein.

To produce a fusion polypeptide with a PHLTS tag, the 90 nucleotide DNA sequence:GGATCCAGATCTGGTAC-CCCTCACCTCACCTCACCTCACCTCACCTCACC T CACCTCACCTCACCTCACCTCACCTCAA-GATCTGAATTC (SEQ ID NO.44) was synthesized by standard methods, cut with the restriction enzymes Bami and EcoRI, and cloned into the vector pGEX-2T (Pharmacia, Piscataway, N.J.) that had been cut with the same two enzymes. The tagged vector was transformed into E. coli DH5 alpha cells and transformants were analyzed by standard methods to confirm that they contained the expected recombinant plasmid. Based on the known sequence of the pGEX-2T plasmid (Smith and Johnson. 1988. Gene 67:31–40) it was expected that the insert would lead to the introduction of the peptide arg ser gly thr pro his leu thr ser pro his leu thr ser pro his leu thr ser pro his leu thr ser arg ser (SEQ ID NO.45) within the GST protein.

Cultures, each 150 ml, of cells containing the tagged pGEX-2T plasmids were grown to mid-log phase and induced with IPTG (3 mM) following standard procedures. After 120 minutes, cells were concentrated by centrifugation. 5 microliters of 5× SDS sample buffer was added to 20 microliters of concentrated cell suspension; boiled for 5 minutes, and clarified by a ten minute centrifugation at 5,000 rpm. 1 microliter samples were loaded onto precast 12.5% acrylamide Pharmacia Phastgels with 6% acrylamide stackers and subjected to SDS gel electrophoresis. Proteins were transferred to PVDF membranes using standard methods. The membranes were blocked with 3% gelatin for 60 minutes and then probed with immune or control sera (1:40 dilution) for 2 hours at room temperature. Reactive antibodies were visualized by standard methods using goat anti-mouse IgG linked to horseradish peroxidase. Each of the nine mouse sera listed in Tables 1 and 2 showed specific reactivity to the appropriate fusion protein, but not to the other fusion protein or to the non-tagged GST protein. Several monoclonal antibodies also showed strong and specific reactivity. An example is shown in FIG. 4.

EXAMPLE 2

Alternative Method for Epitope Tagging

The present invention incorporates by reference U.S. patent application Ser. No. 08/000,619, which is directed to a method whereby a molecular tag is put on a eukaryotic gene, transcript and protein in a single recombinational event. The protein or epitope tag takes the form of a unique peptide that can be recognized by an antibody or other specific reagent. The transcript tag takes the form of the sequence of nucleotides encoding the peptide than can be recognized by a specific polynucleotide probe, and the gene tag takes the form of a larger sequence of nucleotides that includes the peptide-encoding sequence and other associated nucleotide sequences. The DNA which is used for insertion into a target sequence is structured such that when it is inserted into an intron within a gene it creates two hybrid introns separated by a new exon encoding the protein tag. A unique and improved feature of the present invention is directed to the exon, which comprises the oligonucleotide of the present invention encoding for an epitope regardless of the reading frame of the exon. The method allows one to identify new proteins or protein-containing structures, and to readily identify and analyze the genes encoding those protein.

In particular, the present invention is directed to a method of epitope tagging which involves tagging genes, transcripts and proteins in a eukaryotic cell. This method comprises a step of introducing into an intron within a gene a DNA sequence including a first nucleotide sequence, an acceptor site for RNA splicing, a second nucleotide sequence, and a donor site for RNA splicing. The first nucleotide sequence is necessary for splice acceptor function. The second nucleotide sequence, which becomes a "guest exon" when inserted in a target gene, encodes an epitope recognized by an antibody, other reagent or molecule. A further step promotes expression of the gene in a eukaryotic cell to produce a protein product, which comprises a peptide epitope encoded by the second nucleotide sequence as part of its primary structure. A unique aspect of the invention is directed to the second nucleotide sequence, which encodes an epitope independently of the reading frame of the second nucleotide sequence, for example (pro his his thr thr)$_3$ (SEQ ID NO.10).

EXAMPLE 3

Probes

An aspect of the present invention is directed to a probe which has a nucleotide sequence that is sufficiently complementary to an oligonucleotide which comprises a nucleotide sequence which codes for an epitope independently of the reading frame of the nucleotide sequence. As generally understood in the art, a probe is a nucleotide sequence, generally, but not limited to DNA, that is used to detect its homologous location on a target sequence, which may be a chromosome. Probe construction and use are matters of standard technique well known in the literature and incorporated by reference herein.

Probes of the present invention, for example the sequence (TGTGG)$_{12}$ (SEQ ID NO.46) that hybridizes specifically to the sequence (CCACA)$_{12}$ (SEQ ID NO.47) that encodes the (pro his his thr thr)$_3$ (SEQ ID NO.10) epitope tag, are used to detect the presence of the epitope tag by hybridization using standard methods or are used as primers to PCR-amplify sequences lying between two tags or between a tag and a known sequence in a target gene.

EXAMPLE 4

Vectors and, Transformed Host Cells Animals and Plants

The invention provides a recombinant vector which comprises a DNA construct of the invention. As described above, the oligonucleotide of the invention can be inserted into a gene cloned in a specific vector—for example a bacterial plasmid such as pBR322 and its derivitives or the pUC series of plasmids and their derivitives such as pUC118, or a bacterial transposon such as Tn10, Tn5 or Tn3 and their derivitives, or a bacterial virus such as lambda, M13, P22, fl and their derivitives, or a eucaryotic transposon such as Ty-1 or P-element and their derivitives or a eucaryotic virus such as Epstein-Barr virus, herpes virus, baculovirus, adenovirus or SV-40 and their derivitives, or a retrovirus such as MoMLV, MoMSV, ALV and their derivitives, that allows replication and transfer of the oligonucleotide to a host or from one host to another. The vector of the invention is used for introducing the DNA construct of the invention to a host cell, and is useful for producing an aspect of the invention directed to transformed or transgenic cells, animals and plants. Vector construction and use are well known in the scientific literature, which is referenced herein. Techniques are also well known for modifying vectors to accommodate the oligonucleotide of the invention inserted into a target gene for delivery of the target gene into cells.

It is understood that the vectors of the invention are useful for producing animals or plants in which all or a portion of the organism's cells contain a vector of the invention. A transgenic organism is an animal or plant that carries a foreign gene integrated into its genetic material. It is understood that the foreign gene of the invention is a gene that has been tagged by the oligonucleotide of the invention using methods described herein, and which gene is detectable in the transgenic organism using the probe of the invention, or by detecting the polypeptide expression of the tagged gene using the antibodies or other reagents of the invention which are specific for the epitope-tagged polypeptide.

EXAMPLE 5

Method for Purifying a Polypeptide

The invention is directed to a method for purifying a polypeptide. A first step involves tagging a target sequence which encodes a polypeptide with a nucleotide sequence which encodes an epitope independent of the reading frame of the nucleotide sequence to produce a tagged target sequence which encodes a fusion polypeptide. A typical technique for tagging a target sequence is described herein in Example 1. In a subsequent step, the tagged target sequence is expressed in an expression system to produce the fusion polypeptide. Using technques well known in the art (and referenced herein) for purifying polypeptides, the fusion polypeptide is substantially purified. A technique preferred by the invention for purifying a fusion polypeptide involves immunoaffinity chromatography (IAC) (25), which employs antibodies specific for the universal epitope or for the fusion polypeptide which comprises the universal epitope. IAC is a powerful separation procedure for the purificaton of peptide epitopes or fusion polypeptide which comprise a universal epitope. The technique relies upon the immunological specificity of an antibody specific for a universal epitope in terms of the antibodies specific recognition and binding of the epitope, which occurs even in complex mixtures of diverse macromolecules.

IAC is a type of adsorption chromatography. Using IAC, one or more fusion proteins created by the method of the invention in a complex mixture to be separated interact with insoluble particles (the matrix) comprising the chromatographic medium, which is usually packed into a chromatographic column. Unadsorbed components in the mixture remain in the mobile liquid phase, which can then easily separted from the matrix. In one form of IAC, an antibody specific, which is specific for the universal epitope contained in the fusion protein, is immobilized on to the insoluble chromatographic matrix. The corresponding soluble fusion polypeptide in the mixture to be resolved can be specifically adsorbed to the substituted matrix following immunological recognition and binding, and the non-bound moieties (the contaminants) are then simply washed away. The complex between the insoluble immunoadsorbent and antigen is subsequently dissociated and the purified antigen fusion protein obtained.

EXAMPLE 6

Method to Detect a Polypeptide

The invention is directed to a method for detecting a polypeptide, which involves the step of tagging a target sequence which encodes a polypeptide with a nucleotide sequence which encodes an epitope independent of the reading frame of the nucleotide sequence to produce a tagged target sequence which encodes a fusion polypeptide. The tagged target sequence is expressed in an expression system to produce said fusion polypeptide. The expression system is contacted with a sufficient amount of an antibody or reagent which is specific for the epitope under conditions which produce a detectable signal indicating a reaction between the fusion polypeptide and antibody or reagent. Immunoassay methods, which are well known and referenced herein, are used in the present method for detecting a fusion polypeptide. The immunoassay methods employ antibodies specific for the universal epitope or for the fusion polypeptide which comprises the universal epitope. The technique relies upon the immunological specificity of the antibody specific for a universal epitope in terms of the antibodies specific recognition and binding of the epitope, which occurs even in complex mixtures of diverse macromolecules. Competitive assays, two-site (sandwich assays), immunoblotting, and immunocytochemistry are immunoassay methods used in the present method for detecting fusion polypeptides either in complex mixtures, or for detecting expression and location in cells or in multicellular structures of fusion polypeptides by means of immunohistocytochemical methods.

It is intended that all matter contained in the above description or shown in the accompanying drawings shall be interpreted in an illustrative and not limiting sense.

BIBLIOGRAPHY

1. Munro, S. and Pelham, H. R. B., 1984, *EMBO Journal* 3:3087–3093.
2. Wilson, I. A., et al. 1984, *Cell* 37:767–778.
3. Field, J., et al., 1988, *Molec. Cell. Biol.* 8(5): 2159–2165.
4. Munro, S. and Pelham, H. R. B., 1986, *Cell* 46:291–300.
5. Reisdorf, P., et al., 1993, *Current Genetics* 23:181–183.
6. Pati U. K., 1992, *Gene* 114:285–288.
7. Surdez, P. and Jacobs-Lorena, M., 1994, *BioTechniques* 17(3):560–565.
8. Evan, G. I., et al., 1985, *Mol. Cell Biol.* 5:3610–3616.
9. Field, J., et al. 1988, *Molec. Cell Biol.* 8(5):2159–2165.
10. Wilson, I. A., et al., 1984, *Cell,* 37:767–778.
11. *Peptide Antigens, A Practical Approach*, ed. G. B. Wisdom (1994), Oxford University Press, New York, N.Y.
12. *Immunological Recognition of Peptides in Medicine and Biology*, eds. N. D. Zegers, W. J. A. Boersma, and E. Claassen (1995), CRC Press, Boca Raton, Fla.
13. Sugii et al. (1994).
14. Posnett, D. N. and J. P. Tam in *Methods in Immunology*, V. 176:146.
15. Sawin et al. (1992. *J. Cell Science.* 101: 303–313).
16. Surdej and Jacobs-Lorena. 1994. *Biotechniques* 17: 560–565.
17. Ku and Schultz. 1995. *Proc. Nat. Acad. Sci. USA* 92:6552–6556.
18. O'Neil and Hoess. 1995. *Curr. Opin. Struct. Biol.* 5: 443–449.
19. Lu et al., 1995. *Bio/Technology* 13: 366–372.
20. Lebl et al., 1995. *Biopolymers* 37: 177–198.
21. Sepetov et al. 1995. *Proc. Nat. Acad. Sci. USA* 92: 5426–5430.
22. Klug and Famulok. 1994. *Mol. Biol. Rep.* 20: 97–107.
23. Nieuwalandt et al. 1995. *Biochemistry* 34: 5651–5659).
24. Williams et al. 1989. *J. Cell Biol.* 109: 235–245).
25. Jack, G. W., *Mol. Biotechnol.* 1:59–86 (1994).

What is claimed is:

1. An oligonucleotide comprising a nucleotide sequence, said nucleotide sequence encoding an epitope and adapted for insertion into a target nucleotide sequence and for expression in a host cell, said nucleotide sequence encoding said epitope independently of the reading frame of said nucleotide sequence, wherein said nucleotide sequence encoding said epitope has the formula $(S)_n$ wherein S is a sequence of nucleotides whose number is not evenly divisible by 3, and n is an integer equal to or greater than the number of nucleotides in S, with the proviso that upon insertion into said target sequence, said nucleotide sequence does not encode a stop codon in any reading frame.

2. The oligonucleotide of claim 1 further comprising one or more flanking sequences coding for a restriction site, wherein said flanking sequences flank said nucleotide sequence such that the reading frame encoded by said target nucleotide sequence is not broken downstream of said oligonucleotide when said oligonucleotide is inserted into said target nucleotide sequence.

3. A probe having a nucleotide sequence that specifically binds to a nucleotide sequence which codes for an epitope independently of the reading frame of said nucleotide sequence, wherein said nucleotide sequence encoding said epitope has the formula $(S)_n$ wherein S is a sequence of nucleotides whose number is not evenly divisible by 3, and n is an integer equal to or greater than the number of nucleotides in S, with the proviso that upon insertion into said target sequence, said nucleotide sequence does not encode a stop codon in any reading frame.

4. A DNA construct comprising a nucleotide sequence which codes for an epitope independently of the reading frame of said nucleotide sequence, wherein said nucleotide sequence encoding said epitope has the formula $(S)_n$ wherein S is a sequence of nucleotides whose number is not evenly divisible by 3, and n is an integer equal to or greater than the number of nucleotides in S, with the proviso that upon insertion into said target sequence, said nucleotide sequence does not encode a stop codon in any reading frame.

5. The DNA construct of claim 4 further comprising a vector selected from the group of vectors consisting of bacterial plasmids, bacterial transposons, bacterial viruses, eucaryotic transposons and eucaryotic viruses.

6. A vector comprising the DNA construct of claim 4 incorporated into a plasmid for transforming host cells, said plasmid comprising both a drug resistance marker and a replication origin.

7. A vector comprising the DNA construct of claim 4 incorporated into a virus for transforming host cells, said virus selected from the group of viruses consisting of lambda, P22, M13, f1, adenovirus, Epstein-Barr virus, herpes virus, baculovirus, SV-40, MoMLV, MoMSV, ALV, and their derivatives.

8. A vector comprising the DNA construct of claim 4 incorporated into a transposon for transforming host cells, said transposon selected from the group consisting of Tn10, Tn5, Tn3, Ty-1, P element and their derivatives.

9. A host cell transformed with the vector of claim 6.

10. A host cell transformed with the vector of claim 7.

11. A host cell transformed with the vector of claim 8.

* * * * *